US010098829B2

(12) United States Patent
Fisher et al.

(10) Patent No.: US 10,098,829 B2
(45) Date of Patent: *Oct. 16, 2018

(54) LOW WATER METAL ION DENTIFRICE

(75) Inventors: Steven Fisher, Middlesex, NJ (US);
Lynette Zaidel, Cranford, NJ (US);
Michael Prencipe, Princeton Junction, NJ (US)

(73) Assignee: Colgate-Palmolive Company, New York, NY (US)

(*) Notice: Subject to any disclaimer, the term of this patent is extended or adjusted under 35 U.S.C. 154(b) by 167 days.

This patent is subject to a terminal disclaimer.

(21) Appl. No.: 14/116,371

(22) PCT Filed: Jun. 2, 2011

(86) PCT No.: PCT/US2011/038867
§ 371 (c)(1),
(2), (4) Date: Nov. 8, 2013

(87) PCT Pub. No.: WO2012/166142
PCT Pub. Date: Dec. 6, 2012

(65) Prior Publication Data
US 2014/0086851 A1    Mar. 27, 2014

(51) Int. Cl.
*A61K 8/21* (2006.01)
*A61Q 11/00* (2006.01)
*A61K 8/81* (2006.01)
*A61K 8/19* (2006.01)
*A61K 8/24* (2006.01)
*A61K 8/365* (2006.01)
*A61K 8/27* (2006.01)

(52) U.S. Cl.
CPC .............. *A61K 8/8176* (2013.01); *A61K 8/19* (2013.01); *A61K 8/21* (2013.01); *A61K 8/24* (2013.01); *A61K 8/27* (2013.01); *A61K 8/365* (2013.01); *A61Q 11/00* (2013.01); *A61K 2800/48* (2013.01)

(58) Field of Classification Search
CPC . A61K 8/22; A61K 8/24; A61K 8/365; A61K 8/8176; A61Q 11/00
USPC ............................................. 424/49, 57, 401
See application file for complete search history.

(56) References Cited

U.S. PATENT DOCUMENTS

| | | |
|---|---|---|
| 2,946,725 A | 7/1960 | Norris et al. |
| 3,070,510 A | 12/1962 | Cooley et al. |
| 3,538,230 A | 11/1970 | Pader et al. |
| 3,678,154 A | 7/1972 | Widder et al. |
| 3,862,307 A | 1/1975 | Di Giulio |
| 3,959,458 A | 5/1976 | Agricola et al. |
| 4,022,880 A | 5/1977 | Vinson et al. |
| 4,051,234 A | 9/1977 | Gieske et al. |
| 4,206,215 A | 6/1980 | Bailey |
| 4,340,583 A | 7/1982 | Wason |
| 4,627,977 A | 12/1986 | Gaffar et al. |
| 4,647,451 A | 3/1987 | Piechota, Jr. |
| 4,894,220 A | 1/1990 | Nabi et al. |
| 5,000,944 A | 3/1991 | Prencipe et al. |
| 5,004,597 A | 4/1991 | Majeti et al. |
| 5,015,466 A | 5/1991 | Parran, Jr. et al. |
| 5,487,906 A | 1/1996 | Dixit et al. |
| 5,578,293 A | 11/1996 | Prencipe et al. |
| 5,589,160 A | 12/1996 | Rice |
| 5,603,920 A | 2/1997 | Rice |
| 5,651,958 A | 7/1997 | Rice |
| 5,658,553 A | 8/1997 | Rice |
| 5,670,137 A | 9/1997 | Ascione |
| 5,716,601 A | 2/1998 | Rice |
| 5,718,885 A | 2/1998 | Gingold et al. |
| 6,190,644 B1 | 2/2001 | McClanahan et al. |
| 6,667,027 B2 | 12/2003 | Glandorf et al. |
| 6,685,920 B2 | 2/2004 | Baig et al. |
| 6,696,045 B2 | 2/2004 | Yue et al. |
| 6,702,999 B2 | 3/2004 | Lawlor |
| 6,706,277 B2 | 3/2004 | Day et al. |
| 6,713,049 B1 | 3/2004 | White, Jr. et al. |
| 6,719,962 B2 | 4/2004 | Day et al. |
| 6,726,897 B2 | 4/2004 | Lawlor |
| 6,730,291 B2 | 5/2004 | Lawlor |
| 6,821,507 B2 | 11/2004 | Glandorf et al. |
| 6,926,916 B1 | 8/2005 | Day et al. |
| 6,984,376 B2 | 1/2006 | Stephenson et al. |
| 2002/0102220 A1 | 8/2002 | Stephenson |
| 2003/0003061 A1 | 1/2003 | Yue et al. |
| 2007/0071695 A1* | 3/2007 | Chopra et al. .................. 424/53 |
| 2010/0135921 A1* | 6/2010 | Hughes et al. ................. 424/49 |

(Continued)

FOREIGN PATENT DOCUMENTS

| | | |
|---|---|---|
| EP | 0638307 | 11/1997 |
| WO | WO 98/022079 | 5/1998 |
| WO | WO 03/045344 | 6/2003 |
| WO | WO 04/047784 | 6/2004 |
| WO | WO 07/063506 | 6/2007 |

(Continued)

OTHER PUBLICATIONS

BASF, 2010, Insoluble Kollidon® Grades Technical Information.

(Continued)

*Primary Examiner* — Lezah Roberts

(57) ABSTRACT

A dentifrice composition having a low water phase comprising effective amounts of polyphosphate and ionic active ingredients. The composition comprises a source of metal ions, an inorganic phosphate salt having four or more phosphorus atoms and a cross-linked polyvinylpyrrolidone thickening agent in a single phase. Preferred metal ions are stannous, copper and zinc, in particular from zinc citrate and stannous fluoride.

14 Claims, No Drawings

(56) References Cited

U.S. PATENT DOCUMENTS

2010/0135931 A1  6/2010  Baig et al.
2011/0053291 A1  3/2011  Matsuda et al.
2012/0020899 A1* 1/2012  Zaidel .................... A61K 8/25
                                               424/52

FOREIGN PATENT DOCUMENTS

WO    WO 10/105050    9/2010
WO    WO 11/053291    5/2011

OTHER PUBLICATIONS

Crest Pro-Health Enamel Shield, 2011, Mintel GNPD 1522596.
International Search Report and Written Opinion in International Application No. PCT/US2011/038867, dated Mar. 12, 2012.

* cited by examiner

LOW WATER METAL ION DENTIFRICE

FIELD OF THE INVENTION

The present embodiments relate to dentifrice compositions. In particular, the present embodiments relate to dentifrice compositions having a low water phase comprising effective amounts of stannous, copper and zinc ions antimicrobial agents that are formulated with water soluble polyphosphates to reduce astringency and staining associated with these metal ions. The formulations incorporate a thickening agent that is singularly comprised of a cross-linked polyvinylpyrrolidone is effective to provide excellent rheological profile.

BACKGROUND OF THE INVENTION

Polyphosphates have been used in dentifrices to promote oral health. Polyphosphates are known anti-tartar agents that help retard calculus formation. Metal ions such as stannous and zinc ions are known to be effective anti-microbial agents. These metal ions provide anti-gingivitis and anti-plaque benefits and may also improve breath and reduce sensitivity. Stannous fluoride has been used in dentistry since the 1950's as a fluoride source to prevent dental caries. Similarly, zinc citrate has been shown to have anti-plaque, anti-gingivitis and anti-tartar efficacy. In addition, zinc has also shown its efficacy as an anti-malodor agent.

While such actives have previously been used in dentifrices, for several reasons it has proven challenging to provide these actives together in a stable single phase. Once such technical problem is to preserve the bioavailability of stannous ions and maximize the chemical stability of the stannous ion source. Certain polyphosphates are unstable in high aqueous systems. Such polyphosphates in an aqueous system are susceptible to hydrolysis unless they are present at a high pH media, which is not compatible with high stannous availability. Stannous fluoride tends to precipitate metal ions in aqueous environments, thereby reducing the efficacy of the metal ions in the oral care composition. Additionally, the polyphosphates react with ionic fluoride in oral compositions at ambient temperature to produce monofluorophosphate ions and alter the pH of the composition. This reaction compromises the efficacy of the oral composition and its ability to provide stable ionic fluoride and polyphosphate to the oral surfaces.

Other attempts to provide such efficacious dentifrice compositions have reduced the amount of water present in the composition. Reducing the amount of water would theoretically reduce or eliminate the stability issues associated with the fluoride, polyphosphate and other ionic actives. However, reducing the level of water, and optionally replacing some or all of the removed water with a humectant, creates problems in obtaining acceptable rheology and thickening properties in the composition. When water, which is a highly polar solvent, is removed, conventional thickening agents such as carboxymethylcellulose ("CMC") tend to inadequately gel up. Attempts to reduce water content in dentifrice compositions have included the dentifrices described in, e.g., EP 0 638 307 B1; U.S. Pat. No. 4,647,451; and U.S. Pat. No. 5,670,137. Such known formulations have been shown to exhibit progressive thickening over time, which prolongs the time period or even prevents the dentifrice from reaching a rheological steady state. Ideally, dentifrice formulations need to reach a steady state for consumer acceptance within two weeks. If a formulation routinely increases in viscosity over time, dispensing of the formulation will become difficult, which will likely result in consumer dissatisfaction.

The description herein of certain advantages and disadvantages of known compositions, methods, and apparatus is not intended to limit the scope of the embodiments to their exclusion (or inclusion, as the case may be). Indeed, certain embodiments may include one or more known compounds, methods, or apparatus without suffering from the aforementioned disadvantages.

BRIEF SUMMARY

There is a need in the art to provide dentifrice compositions that can effectively combine sources of stannous, fluoride, and zinc ions in combination with a polyphosphate having four or greater phosphorus atoms in a low water single phase system that has efficacious delivery of water-unstable actives and/or actives that are reactive with respect to each other in a single phase. There is also a need to provide low water single phase dentifrice compositions that have an improved rheological profile.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE EMBODIMENTS

The following description of the preferred embodiment(s) is merely exemplary in nature and is in no way intended to limit the invention, its application, or uses. All percentages used herein are by weight of the total dentifrice composition, unless otherwise specified. The ratios used herein are weight ratios of the respective components, unless otherwise specified. All measurements are made at 25° C., unless otherwise specified. As used throughout, ranges are used as a shorthand for describing each and every value that is within the range. Any value within the range can be selected as the terminus of the range.

A dentifrice composition is a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity. A dentifrice composition of the present invention may be in the form of a toothpaste or dentifrice. The term "dentifrice," as used herein, means paste or gel formulations unless otherwise specified. The dentifrice composition may be in any desired form, such as deep striped, surface striped, multi-layered, having the gel surrounding the paste, or any combination thereof.

The phrase "aqueous carrier" as used herein means any safe and effective materials for use in the compositions of the present embodiments. Such materials include thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

The embodiments described herein relate to a dentifrice composition having a phase with a low water content and containing an orally acceptable vehicle, a source of fluoride ions, a source of stannous ions, a source of zinc ions, and at least one polyphosphate salt. The polyphosphate salt may be inorganic polyphosphate salts which have four or more phosphorous atoms. The dentifrice composition may have a total water content of less than about 6% based on the weight of the composition.

The vehicle may include a thickening agent comprising at least one of a cross-linked polyvinylpyrrolidone. The cross-linked polyvinylpyrrolidone may comprise a homopolymer of N-vinyl-2-pyrrolidone. The cross-linked polyvinylpyrrolidone may comprise from 0.05 to 15 wt % of the composition, preferably from 0.75 to 1.25 wt % of the composition.

The at least one polyphosphate may be selected from the group consisting of an alkali metal salt of a tetraphosphate, preferably the at least one polyphosphate is selected from the group consisting of hexasodium tetraphosphate or sodium hexametaphosphate. The at least one polyphosphate may comprise a mixture of hexasodium tetraphosphate and sodium hexametaphosphate, and preferably the mixture of hexasodium tetraphosphate and sodium hexametaphosphate comprises the hexasodium tetraphosphate and sodium hexametaphosphate in about a 2:3 weight ratio. The at least one polyphosphate may comprise from 1 to 10 wt % of the composition, preferably from 3 to 7 wt % of the composition.

Preferably, the source of fluoride ions and the source of stannous ions comprise stannous fluoride. Preferably, the source of zinc ions comprises a zinc salt of an organic acid, more preferably zinc citrate. The source of zinc ions may also comprise any zinc compound including, for example, zinc oxide, zinc tartrate, zinc gluconate, and the like.

In the dentifrice composition, the composition may further comprise at least one humectant selected from the group consisting of glycerin, polyethylene glycol, propylene glycol, and mixtures thereof.

Preferably, the composition further comprises an aqueous buffer system for the source of stannous ions. The buffer system preferably is adapted to chelate the stannous ions in the composition. The buffer system may comprise at least one of an organic acid or an alkali metal salt thereof, the organic acid preferably being citric acid. The buffer system may comprise a mixture of citric acid and trisodium citrate. The buffer system may comprise from 1 to 5 wt % of the composition. The buffer system may be present, by weight, in an amount that is greater than the amount, by weight, of the source of stannous ions.

The present invention also provides a dentifrice composition comprising, in a single phase, an orally acceptable vehicle, the vehicle including a thickening agent comprising a thickening agent comprising a cross-linked polyvinylpyrrolidone, wherein the dentifrice composition has a total water content of less than about 10% based on the weight of the composition.

While not intending on being bound by any theory of operation, the present inventors believe that a particular thickening system, which employs a cross-linked polyvinylpyrrolidone enables a single phase low water dentifrice composition to achieve a viscosity that is substantially constant and that is sufficiently low to permit the dentifrice composition readily to be dispensed over a long shelf life. Without being bound by any theory, it is believed that the cross-linked polyvinylpyrrolidone permits the polyvinylpyrrolidone polymer thickener to be readily hydrated in the low water system, which allows substantially complete initial hydration of the polymer during manufacture of the dentifrice composition.

The embodiments described herein provide a dentifrice composition comprising in a single phase: an orally acceptable vehicle; a source of fluoride ions; a source of stannous ions; a source of zinc ions; and at least one polyphosphate salt selected from the group consisting of inorganic polyphosphate salts that have four or greater phosphorous atoms; wherein the dentifrice composition has a total water content of less than about 10% based on the weight of the composition.

As will be demonstrated herein, the preferred embodiments can provide a dentifrice that provides multiple therapeutic benefits by combining stannous ions and fluoride ions, e.g. as stannous fluoride, zinc ions, e.g. as zinc citrate, and polyphosphates, e.g. in the form of hexasodium tetraphosphate/sodium hexametaphosphate. The use of a particular buffer system can stabilize the stannous ions in the presence of the zinc ions and polyphosphates, and leave the stannous ions active in the single phase low water composition for effective anti-microbial action when used for cleaning the teeth.

The preferred embodiments of the present invention also can provide a dentifrice formulation having a stabilized stannous ion source and a polyphosphate, for example hexasodium tetraphosphate and/or sodium hexametaphosphate, in a single tube.

The preferred embodiments of the present invention also can provide a low water dentifrice system combining, in a single tube, stannous fluoride, zinc citrate and polyphosphates, in particular having a phosphorous atom of equal to or greater than four, for example tetraphosphate and/or sodium hexametaphosphate, in a single phase system that provides bioavailable tin, zinc, fluoride and polyphosphate to the oral surfaces.

While the specification concludes with claims particularly pointing out and distinctly claiming the invention, it is believed that the present invention will be better understood from the following description of preferred embodiments.

Polyphosphate Source

The present embodiments may include a polyphosphate source. Polyphosphates are known to help retard calculus formation. However, it is also known that polyphosphates with an average chain length four or greater will also react with ionic fluoride in oral compositions at ambient temperature and produce monofluorophosphate ions, in addition to altering the pH of the composition. This reaction may compromise the efficacy of the oral composition and its ability to provide stable ionic fluoride and polyphosphate to the oral surfaces. It also is known that to have stable polyphosphate, the total water content and pH of the dentifrice composition should be controlled to reduce the hydrolysis of the polyphosphate.

A polyphosphate generally is understood to consist of two or more phosphate molecules arranged primarily in a linear configuration, although some cyclic derivatives may be present. The preferred inorganic polyphosphate salts, which are preferably alkali metal salts, used in the dentifrice compositions of the present invention have four or more phosphorous atoms, such as a tetraphosphate, for example hexasodium tetraphosphate, or a polyphosphate, for example sodium hexametaphosphate. These polyphosphates may be used alone or in any combination thereof.

An effective amount of a polyphosphate source may be from about 0.1% to about 30%, preferably from about 1% to about 26%, more preferably from about 4% to about 20%, and most preferably from about 5% to about 13%, by weight of the total dentifrice composition. A typical range is from about 1% to about 10% by weight of the total dentifrice composition, more typically from about 3% to about 7% by weight of the total dentifrice composition.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. Aqueous carriers typically comprise from about 40% to about 99%, preferably from about 70% to about 98%, and more preferably from about 90% to about 95%, by weight of the dentifrice composition.

Total Water Content

Water employed in the preparation of commercially suitable oral compositions should preferably be of low ion content and free of organic impurities. In the dentifrice composition, water will generally comprise less than about 6%, and preferably from about 0% to less than 4%, by weight of the composition herein. Polyphosphate and actives such as fluoride and stannous are not dissolved in the compositions herein in such low levels of water. However, these ingredients may be dissolved in the present compositions in other low polar solvents, forming non-ionic molecular structures. In either case, the actives remain stable in the compositions during storage. The fluoride ion and the stannous ion if present will be released from their salt forms or non-ionic solution forms when contacted with saliva and/or water at the time of brushing. Thus there is no need to physically separate the polyphosphate-containing portion of the composition from the ionic active-containing portion of the composition, for example by using a dual compartmented package. In addition, fluoride ion from a variety of sources may be used efficaciously in the present composition; there is no preference for the use of sodium monofluorophosphate as the fluoride ion source that is most compatible with the polyphosphate in the composition as previously described in U.S. Pat. No. 6,190,644, "Dentifrice Compositions Containing Polyphosphate and Sodium Monofluorophosphate."

The amounts of water include the free water that is added plus that which is introduced with other materials, such as with silica, surfactant solutions, and/or color solutions.

Humectant

The humectant serves to keep toothpaste compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. Preferred are glycerin, polyethylene glycol, polypropylene glycol, and mixtures thereof, especially mixtures thereof. The humectant generally comprises from about 0.1% to 70%, preferably from about 1% to about 60%, and more preferably from about 15% to 55%, by weight of the composition.

The humectant is believed to have a significant impact on the viscosity of the low water matrix. For example, when using polysaccharide as the thickening agent in the composition, the viscosity of the matrix will increase when the level of glycerin or polyethylene glycol increases. On the contrary, the viscosity of matrix will decrease when the level of propylene glycol increases in the composition.

Ionic Active Ingredient

The dentifrice compositions of the present invention preferably comprise an effective amount of an ionic active ingredient selected from the group consisting of a fluoride ion source, a stannous ion source, a zinc ion source, and mixtures thereof.

Fluoride Ion Source

The fluoride ion source herein is a soluble fluoride source capable of providing free fluoride ions. Soluble fluoride ion sources include sodium fluoride, stannous fluoride, indium fluoride, zinc fluoride, and sodium monofluorophosphate. Sodium fluoride and stannous fluoride are the preferred soluble fluoride ion sources. Norris et al., U.S. Pat. No. 2,946,725, issued Jul. 26, 1960, and Widder et al., U.S. Pat. No. 3,678,154 issued Jul. 18, 1972, disclose such fluoride ion sources as well as others.

The fluoride ion source in the present compositions preferably is present as a solid dispersion in the composition during storage, prior to actual brushing usage of the composition by a consumer. The level of water in the present compositions is too low to permit the fluoride source to dissolve in the composition during storage. Thus, there is no obvious interaction between the fluoride ion and the polyphosphate, or silica if present, during storage, providing a stable composition during storage. When the composition is contacted by saliva and/or water at the time of brushing, the fluoride source preferably will be dispersed and the active ion will be delivered to the oral cavity.

The present compositions may contain a soluble fluoride ion source capable of providing from about 50 ppm to about 3500 ppm, and preferably from about 500 ppm to about 3000 ppm of free fluoride ions. To deliver the desired amount of fluoride ions, fluoride ion source may be present in the total dentifrice composition at an amount of from about 0.1% to about 5%, preferably from about 0.2% to about 1%, and more preferably from about 0.3 to about 0.6%, by weight of the total dentifrice composition.

Metal Ion Source

The present invention may comprise a metal ion source that provides stannous ions, zinc ions, copper ions or mixtures thereof. The metal ion source can be a soluble or a sparingly soluble compound of stannous or zinc with inorganic or organic counter ions. Examples include the fluoride, chloride, chlorofluoride, acetate, hexafluorozirconate, sulfate, tartrate, gluconate, citrate, malate, glycinate, pyrophosphate, metaphosphate, oxalate, phosphate, carbonate salts and oxides of stannous and zinc. Metal ion sources include copper bisglycinate, copper glycinate, zinc citrate, and zinc lactate.

Stannous and zinc ions have been found to help in the reduction of gingivitis, plaque, sensitivity, and improved breath benefits. The efficacy of these metal ions in the present compositions is not reduced by the polyphosphate.

Stannous and zinc ions are derived from the metal ion source(s) found in the dentifrice composition in an effective amount. An effective amount is defined as from at least about 1000 ppm metal ion, preferably about 2,000 ppm to about 15,000 ppm. More preferably, metal ions are present in an amount from about 3,000 ppm to about 13,000 ppm and even more preferably from about 4,000 ppm to about 10,000 ppm. This is the total amount of metal ions (stannous and zinc and mixtures thereof) that is present in the compositions for delivery to the tooth surface.

The metal ion sources in the present compositions are preferably not fully ionized in the composition during storage, prior to actual brushing usage of the composition by a consumer. The level of water in the present compositions is too low to permit the metal ion source to dissolve in the composition during storage. But certain salts such as stannous chloride and stannous fluoride, can be solubilized in glycerin or propylene glycol. Both humectants can provide super stability protection for such stannous salts and also can provide a better taste profile than a water (aqueous) solution of stannous. When the composition is contacted by saliva and/or water at the time of brushing, the stannous ion source will be fully ionized and the active ion will be delivered to the oral cavity.

Dentifrices containing stannous salts, particularly stannous fluoride and stannous chloride, are described in U.S. Pat. No. 5,004,597 to Majeti et al. Other descriptions of stannous salt dentifrices are found in U.S. Pat. No. 5,578,293. The preferred stannous salts are stannous fluoride and stannous chloride dihydrate. Other suitable stannous salts include stannous acetate, stannous tartrate and sodium stannous citrate. Examples of suitable zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880.

The combined metal ion source(s) will be present in an amount of from about 0.25% to about 11%, by weight of the final composition. Preferably, the metal ion sources are present in an amount of from about 0.4 to about 7%, more preferably from about 0.45% to about 5%.

Buffering Agent

The compositions described herein also may contain a buffering agent in addition to the chelating buffer agent for the stannous ions that is used in a premix as described hereinabove. Buffering agents, as used herein, refer to agents that can be used to adjust the pH of the compositions to a range of about pH 3.0 to about pH 10. The phase of the dentifrice containing stannous will typically have a slurry pH of from about 3.0 to about 5.5, preferably from about 3.25 to about 5, and more preferably from about 3.4 to about 4.5. The phase of the dentifrice containing the polyphosphate will typically have a slurry pH of from about 4.0 to about 10, preferably from about 4.5 to about 8, and more preferably from about 5.0 to about 7.0. A dentifrice containing both stannous and polyphosphate in a single phase will typically have a pH of from about 4 to about 7, preferably from about 4.5 to about 6, and more preferably from about 5 to about 5.5.

The buffering agents include alkali metal hydroxides, ammonium hydroxide, organic ammonium compounds, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Buffering agents are used at a level of from about 0.1% to about 30%, preferably from about 0.1% to about 10%, and more preferably from about 0.3% to about 3%, by weight of the present composition. When stannous is present in the composition, preferred buffers are sodium hydroxide, potassium hydroxide, and ammonium hydroxide.

Anticalculus Agents

The compositions described herein also may employ, as anticalculus agents, polyphosphate materials known to be effective in reducing calcium phosphate mineral deposition related to calculus formation. Agents included are pyrophosphates, and tripolyphosphates. The compositions may also employ synthetic anionic polymers [including polyacrylates and copolymers of maleic anhydride or acid and methyl vinyl ether (e.g., GANTREZ®), as described, for example, in U.S. Pat. No. 4,627,977 to Gaffar et al.; as well as, e.g., polyamino propane sulfonic acid (AMPS)], zinc citrate trihydrate, diphosphonates (e.g., EHDP; AHP), polypeptides (such as polyaspartic and polyglutamic acids), and mixtures thereof.

Abrasive Polishing Materials

An abrasive polishing material may also be included in the toothpaste compositions. The abrasive polishing material contemplated for use in the compositions of the present invention can be any material that does not excessively abrade dentin. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962. Mixtures of abrasives may also be, used. If the dentifrice composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975. Preferred are the silica xerogels marketed under the trade name "SYLOID®" by the W. R. Grace & Company, Davison Chemical Division. Also preferred are the precipitated silica materials such as those marketed by the J. M. Huber Corporation under the trade name, "ZEODENT®", particularly the silica carrying the designation "Zeodent 119." The types of silica dental abrasives useful in the toothpastes of the present invention are described in more detail in Wason, U.S. Pat. No. 4,340,583, issued Jul. 29, 1982. Silica abrasives are also described in Rice, U.S. Pat. Nos. 5,589,160; 5,603,920; 5,651,958; 5,658,553; and 5,716,601. The abrasive in the toothpaste compositions described herein is generally present at a level of from about 6% to about 70% by weight of the composition. Preferably, toothpastes contain from about 10% to about 50% of abrasive, by weight of the dentifrice composition.

Peroxide Source

The present invention may include a peroxide source in the composition. The peroxide source is selected from the group consisting of hydrogen peroxide, calcium peroxide, urea peroxide, and mixtures thereof. The preferred peroxide source is calcium peroxide. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the dentifrice composition.

Alkali Metal Bicarbonate Salt

The compositions also may include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. The present composition may contain from about 0.5% to about 50%, preferably from about 0.5% to about 30%, more preferably from about 2% to about 20%, and most preferably from about 5% to about 18% of an alkali metal bicarbonate salt, by weight of the dentifrice composition.

Additional Aqueous Carriers

The compositions also may comprise surfactants, also commonly referred to as sudsing agents. Suitable surfactants are those that are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the paramenthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents, such as additional antimicrobial agents. Included among such agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides, polyphenols, and herbals. The water soluble antimicrobials include quaternary ammonium salts and bis-biquanide salts, among others. Triclosan monophosphate is a preferred additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis[4-(R-amino)-1-pyridinium] alkanes as disclosed in U.S. Pat. No. 4,206,215, issued Jun. 3, 1980, to Bailey.

Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, Sep. 27, 1977 to Gieske et al. Specific antimicrobial agents include chlorhexidine, triclosan, triclosan monophosphate, and flavor oils such as thymol. Triclosan is a preferred antimicrobial agent for inclusion in the present compositions. Triclosan and other agents of this type are disclosed in Parran, Jr. et al., U.S. Pat. No. 5,015,466, issued May 14, 1991, and U.S. Pat. No. 4,894,220, Jan. 16, 1990 to Nabi et al. The water insoluble antimicrobial agents, water soluble agents, and enzymes may be present in either the first or second dentifrice compositions. The quaternary ammonium agents, stannous salts, and substituted guanidines are preferably present in the second dentifrice composition. These agents may be present at levels of from about 0.01% to about 1.5%, by weight of the dentifrice composition.

A herbal agent, including but not limited to, golden thread extract, honeysuckle extract, and mixtures thereof, may also be present in the compositions herein at levels of from about 0.01% to about 0.05%. Such herbal agents are believed to provide anti-bacterial efficacy. Polyphenols may further be included at levels from about 0.01% to about 2%. A preferred polyphenol is tea polyphenol.

An effective amount of a desensitizing agent may also be incorporated into the present compositions. The desensitizing agents include those selected from alkaline metal salts with a chloride, nitrate sulfate, or acetate of a group II metal or aluminum or polymerizable monomer to occlude the tubules, alkaline metal or ammonium nitrate, ammonium oxylate, citric acid and sodium citrate. Preferred salts are potassium nitrate, potassium citrate, and mixtures thereof. Such desensitizing agents are disclosed in e.g., U.S. Pat. No. 5,718,885.

For compositions that contain stannous, a stain reducing agent such as polyvinyl pyrrolidone (PVP) or aluminum hydrate may further be added to the composition. PVP can have preferably a mean molecular weight ranging from 10,000 to 700,000. Herein, the low molecular weights and middle molecular weights (from about 10,000 to about 100,000) are preferred. In order to remove stain effectively, the level of PVP is preferably from about 0.5% to about 10%, more preferably from about 1.0% to about 7.0%, and even more preferably from about 1.5% to about 5.0%.

The dentifrice compositions may be a paste, gel, or any configuration or combination thereof. The dispenser for the dentifrice compositions may be a tube, pump, or any other container suitable for dispensing toothpaste.

Methods of Use

In practicing the embodiments, the user need only apply the dentifrice composition herein, to the tooth surfaces of a human or animal, in the areas desired, in order to obtain a desired effect, e.g., whitening, breath freshening, caries prevention, pain relief, gum health, tartar control, erosion control, etc. Use of dentifrices to control erosion of the tooth surface, or to prevent demineralization, are known and described in, for example, U.S. Pat. No. 6,685,920, the disclosure of which is incorporated by reference herein in its entirety. The compositions also may be applied to other oral cavity surfaces, such as the gingival or mucosal tissues, although it is believed that the benefits are best achieved when the dentifrice compositions are applied to the teeth. The dentifrice composition may contact the tooth and/or oral cavity surface either directly, or indirectly, however, it is preferred that the dentifrice composition be directly applied. The dentifrice composition may be applied by any means, but is preferably applied with a brush or by rinsing with a dentifrice slurry.

The manufacture of the oral composition of the present invention may be accomplished by any of the various standard techniques for producing such compositions. To make a dentifrice, a vehicle may be prepared containing humectant, for example, one or more of glycerin, glycerol, sorbitol, and propylene glycol, thickener agents and antibacterial agent, and the vehicle, followed by blending in of a polishing agent, as well as fluoride salts, with the pre-mix. Finally, flavoring agent, is admixed and the pH is adjusted to between 6.8 to 7.0.

The following examples are further illustrative of the preferred embodiments, but it is understood that the invention is not limited thereto.

Example 1

Dentifrice compositions were prepared having the formulations as indicated in Table 1.

TABLE 1

| INGREDIENT | Formula A | Formula B |
| --- | --- | --- |
| Polyethylene glycol 600 | 10 | 10 |
| Glycerin | 49.946 | 49.946 |
| Hexametapyrophosphate | 8 | 8 |
| Stannous fluoride | 0.454 | 0.454 |
| Zinc citrate | 2 | 2 |
| Deionized water | 3 | 3 |
| Sodium saccharin | 0.3 | 0.3 |
| Crospovidone | 4.5 | 0 |
| Carrageenan | 0 | 4.0 |
| Xanthan | 0 | 0.5 |
| Zeodent 114 | 15 | 15 |
| Zeodent 165 | 3 | 3 |
| Titanium dioxide | 1 | 1 |
| Sodium lauryl sulfate | 1.5 | 1.5 |
| Flavor | 1.3 | 1.3 |
| TOTAL | 100 | 100 |
| Rheology (cps) | 191,400 | 46,400 |

Each of the formulations contain 0.454 wt % stannous fluoride, 2 wt % zinc citrate and a polyphosphate anti-tartar control system, comprising 8 wt % hexametaphosphate.

The compositions in accordance with Formula A and Formula B incorporated different thickener systems. The formulations were subjected to a rheology test to determine viscosity. The viscosity of each formulation was determined with a Brookfield Viscometer Model RVT or RVTDV attached to a Brookfield Helipath Stand utilizing a RV T-Bar Spindle Set. Viscosity profiles were recorded on a linear 1200 recorder. (Brookfield Engineering Laboratories, Stoughton, Ma.) Brookfield viscosity of the composition was taken at ambient conditions and the results are shown in Table 1. It may be seen that the prior art thickeners produced a product that lacked suitable viscosity levels whereas the product made in accordance with the invention has suitable viscosity levels.

It may be seen therefore that the thickening composition employed in accordance with the preferred embodiments of the present invention enabled a useful rheological state to be reached.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

What is claimed is:

1. A low water dentifrice composition comprising in a single phase:
   a source of metal ions;
   at least one polyphosphate salt selected from the group consisting of inorganic polyphosphate salts which have four or more phosphorous atoms; and
   a thickening agent comprising a cross-linked polyvinylpyrrolidone;
   wherein the dentifrice composition is a paste or gel, wherein the dentifrice composition has a total water content of 3% to 10% based on the weight of the composition, and wherein the at least one polyphosphate salt comprises from 1 to 10 wt % of the composition; and
   wherein the source of metal ions comprises zinc citrate and stannous fluoride present in a combined amount of from 0.45 to 5% by weight of the composition;
   wherein the cross-linked polyvinylpyrrolidone is present in an amount of 0.05 to 15% by weight of the composition;
   wherein the composition does not comprise a peroxide source, and does not comprise a pyrophosphate or tripolyphosphate.

2. The composition of claim 1, wherein the thickening agent consists essentially of a cross-linked polyvinylpyrrolidone.

3. The composition of claim 1, wherein the at least one polyphosphate is an alkali metal salt of a hexametaphosphate.

4. The composition of claim 3, wherein the at least one polyphosphate is sodium hexametaphosphate.

5. The composition of claim 1, wherein the at least one polyphosphate salt comprises from 3 to 7 wt % of the composition.

6. The composition of claim 1, wherein the dentifrice composition has a total water content of 3% to 4% based on the weight of the composition.

7. The composition of claim 1, further comprising an aqueous buffer system for the source of metal ions.

8. The composition of claim 7, wherein the buffer system is adapted to chelate the metal ions in the composition.

9. The composition of claim 8, wherein the buffer system comprises at least one of an organic acid or an alkali metal salt thereof.

10. The composition of claim 9, wherein the organic acid is citric acid.

11. The composition of claim 9, wherein the buffer system comprises a mixture of citric acid and trisodium citrate.

12. The composition of claim 9, wherein the buffer system comprises from 0.1 to 10 wt % of the composition.

13. The composition of claim 9, wherein the buffer system is present, by weight, in an amount which is greater than the amount, by weight, of the source of metal ions.

14. The composition of claim 1, wherein the at least one polyphosphate is an alkali metal salt of a tetraphosphate.

* * * * *